(12) United States Patent
Pierson et al.

(10) Patent No.: US 7,959,370 B2
(45) Date of Patent: Jun. 14, 2011

(54) PACKAGED DENTAL COMPOSITION

(75) Inventors: Paul R. Pierson, Camden, DE (US); Paul D. Hammesfahr, Wyoming, DE (US)

(73) Assignee: Dentsply International, Inc., York, PA (US)

( * ) Notice: Subject to any disclaimer, the term of this patent is extended or adjusted under 35 U.S.C. 154(b) by 313 days.

(21) Appl. No.: 12/284,072

(22) Filed: Sep. 18, 2008

(65) Prior Publication Data

US 2009/0020440 A1     Jan. 22, 2009

Related U.S. Application Data (63) Continuation of application No. 11/586,798, filed on Oct. 26, 2006, now abandoned, which is a continuation of application No. 11/146,975, filed on Jun. 7, 2005, now abandoned, and a continuation of application No. 10/668,946, filed on Sep. 23, 2003, now abandoned.

(60) Provisional application No. 60/319,581, filed on Sep. 27, 2002.

(51) Int. Cl.
*B43K 5/14* (2006.01)

(52) U.S. Cl. .................... 401/132; 401/126; 433/141

(58) Field of Classification Search ................ 401/123, 401/126, 128, 129, 130, 132; 433/141, 146; 604/1–3
See application file for complete search history.

(56) References Cited

U.S. PATENT DOCUMENTS

| | | |
|---|---|---|
| 1,259,964 A | 3/1918 | Davis |
| 1,382,163 A | 6/1921 | Beccari |
| 2,605,937 A | 8/1952 | Bradley |
| 2,826,339 A | 3/1958 | Maillard |
| 3,166,221 A | 1/1965 | Nielsen |
| 3,262,608 A | 7/1966 | Macey |
| 3,330,444 A | 7/1967 | Raypholtz |
| 3,356,244 A | 12/1967 | Witchell |
| 3,595,439 A | 7/1971 | Newby et al. |
| 3,767,085 A | 10/1973 | Cannon et al. |
| 4,215,985 A | 8/1980 | Madlener |
| 4,457,818 A | 7/1984 | Denyer et al. |
| 4,500,657 A | 2/1985 | Kumar |
| 4,502,616 A | 3/1985 | Meierhoefer |
| 4,515,267 A | 5/1985 | Welsh |
| 4,525,256 A | 6/1985 | Martin |
| 4,538,920 A | 9/1985 | Drake |
| 4,540,723 A | 9/1985 | Ying |
| 4,566,413 A | 1/1986 | Maly |
| 4,648,532 A | 3/1987 | Green |
| 4,708,650 A | 11/1987 | Holewinski et al. |
| 4,732,287 A | 3/1988 | Bennett |
| 4,753,536 A | 6/1988 | Spehar et al. |
| 4,767,026 A | 8/1988 | Keller et al. |

(Continued)

FOREIGN PATENT DOCUMENTS

AU     4205193     3/1994

(Continued)

*Primary Examiner* — David J Walczak
(74) *Attorney, Agent, or Firm* — Douglas J. Hura; David A. Zdurne; Leana Levin (57) ABSTRACT

A container enclosing an applicator and a dental composition including a volatile organic solvent. The container is sealed. The volatile organic solvent is effectively retained within the container, even after storage at about 43° C. for one week. Preferably the container is made of a copolymer of a cycloolefin and an open chain olefin.

29 Claims, 13 Drawing Sheets

U.S. PATENT DOCUMENTS

| | | |
|---|---|---|
| 4,767,326 A | 8/1988 | Bennett et al. |
| 4,776,704 A | 10/1988 | Kopunek et al. |
| 4,811,549 A | 3/1989 | Usami et al. |
| 4,844,251 A | 7/1989 | Gueret |
| 4,869,400 A | 9/1989 | Jacobs |
| 4,880,111 A | 11/1989 | Bagwell et al. |
| 4,950,237 A | 8/1990 | Henault et al. |
| 4,952,068 A | 8/1990 | Flint |
| 4,952,204 A | 8/1990 | Korteweg |
| 4,972,969 A | 11/1990 | Randklev |
| 4,995,519 A | 2/1991 | Rose et al. |
| 4,995,540 A | 2/1991 | Colin et al. |
| 4,997,371 A | 3/1991 | Fischer |
| 5,004,124 A | 4/1991 | Stefaniak et al. |
| 5,033,650 A | 7/1991 | Colin et al. |
| RE33,801 E | 1/1992 | Green |
| 5,080,589 A | 1/1992 | Oden et al. |
| 5,125,837 A | 6/1992 | Warrin et al. |
| 5,137,178 A | 8/1992 | Stokes et al. |
| 5,172,807 A | 12/1992 | Dragan et al. |
| 5,195,663 A | 3/1993 | Martin et al. |
| 5,197,496 A | 3/1993 | Nakamura |
| 5,246,371 A | 9/1993 | Fischer |
| 5,267,859 A | 12/1993 | Discko, Jr. |
| 5,269,684 A | 12/1993 | Fischer |
| 5,273,190 A | 12/1993 | Lund |
| 5,286,257 A | 2/1994 | Fischer |
| 5,295,615 A | 3/1994 | Gentile |
| 5,324,273 A | 6/1994 | Discko, Jr. |
| 5,326,164 A | 7/1994 | Logan |
| 5,333,760 A | 8/1994 | Simmen |
| 5,336,088 A | 8/1994 | Discko, Jr. |
| 5,382,162 A | 1/1995 | Sharp |
| 5,401,169 A | 3/1995 | Fleisher et al. |
| 5,419,703 A | 5/1995 | Warrin et al. |
| 5,443,182 A | 8/1995 | Tanaka et al. |
| 5,501,371 A | 3/1996 | Schwartz-Feldman |
| 5,554,665 A | 9/1996 | Tateosian et al. |
| 5,584,815 A | 12/1996 | Pawelka et al. |
| 5,609,271 A | 3/1997 | Keller et al. |
| 5,616,337 A | 4/1997 | Kasianovitz et al. |
| 5,624,260 A | 4/1997 | Wilcox et al. |
| 5,660,273 A | 8/1997 | Discko, Jr. |
| 5,676,280 A | 10/1997 | Robinson |
| 5,695,340 A | 12/1997 | Lee et al. |
| 5,697,524 A | 12/1997 | Sedlmeier |
| 5,707,234 A | 1/1998 | Bender |
| 5,710,194 A | 1/1998 | Hammesfahr et al. |
| 5,716,150 A | 2/1998 | Gueret |
| 5,722,829 A | 3/1998 | Wilcox et al. |
| 5,725,499 A | 3/1998 | Silverstein et al. |
| 5,743,436 A | 4/1998 | Wilcox et al. |
| 5,788,122 A | 8/1998 | Keller |
| 5,816,804 A | 10/1998 | Fischer |
| 5,819,921 A | 10/1998 | Schmid |
| 5,819,988 A | 10/1998 | Sawhney et al. |
| 5,829,976 A | 11/1998 | Green |
| 5,848,894 A | 12/1998 | Rogers |
| 5,860,806 A | 1/1999 | Pranitis, Jr. et al. |
| 5,871,355 A | 2/1999 | Dragan et al. |
| 5,875,791 A | 3/1999 | Sheffler et al. |
| RE36,235 E | 6/1999 | Keller et al. |
| 5,924,600 A | 7/1999 | Keller |
| 5,947,622 A | 9/1999 | Akyildiz et al. |
| 6,033,143 A | 3/2000 | Gueret |
| 6,048,201 A | 4/2000 | Zwingenberger |
| 6,059,473 A | 5/2000 | Gueret |
| 6,059,570 A | 5/2000 | Dragan et al. |
| 6,065,645 A | 5/2000 | Sawhney et al. |
| 6,079,871 A | 6/2000 | Jona et al. |
| 6,082,999 A | 7/2000 | Tcherny et al. |
| 6,592,280 B2 * | 7/2003 | Petrich et al. .................. 401/126 |

FOREIGN PATENT DOCUMENTS

| | | |
|---|---|---|
| AU | 667375 | 3/1996 |
| CA | 2101137 | 3/1994 |
| DE | 3122237 | 1/1983 |
| DE | 3310215 | 9/1984 |
| DE | 3717512 | 12/1987 |
| DE | 9202654 | 6/1992 |
| DE | 9303268 | 8/1994 |
| DE | 4418682 | 11/1995 |
| DE | 19628552 | 2/1997 |
| DE | 19648820 | 5/1998 |
| DE | 19706932 | 8/1998 |
| DE | 19722765 | 12/1998 |
| DE | 69322612D | 1/1999 |
| DE | 69322612 T | 7/1999 |
| EP | 0049553 | 4/1982 |
| EP | 0156464 | 10/1985 |
| EP | 0237182 | 9/1987 |
| EP | 0283164 | 9/1988 |
| EP | 0319639 | 6/1989 |
| EP | 0407870 | 1/1991 |
| EP | 0608598 | 8/1994 |
| EP | 0411578 | 11/1994 |
| EP | 0895943 | 2/1999 |
| EP | 0919206 | 6/1999 |
| EP | 1121905 | 8/2001 |
| ES | 2127791 T | 5/1999 |
| GB | 842965 | 8/1960 |
| GB | 1527544 | 10/1978 |
| JP | 6-169941 | 6/1994 |

\* cited by examiner

PACKAGED DENTAL COMPOSITION

RELATED APPLICATIONS

This application is a Continuation application of U.S. patent application Ser. No. 11/586,798 filed Oct. 26, 2006, now abandoned, which is a Continuation application of U.S. patent application Ser. No. 11/146,975 filed Jun. 7, 2005, now abandoned, which is a Continuation application of U.S. patent application Ser. No. 10/668,946 filed Sep. 23, 2003, now abandoned, which claims the benefit from Provisional Application No. 60/319,581 filed Sep. 27, 2002.

TECHNICAL FIELD

The invention relates to packaged dental compositions. In accordance with the invention is provided a container enclosing an applicator and a dental composition having one or more volatile components.

DETAILED DESCRIPTION OF THE INVENTION

Figure 1:
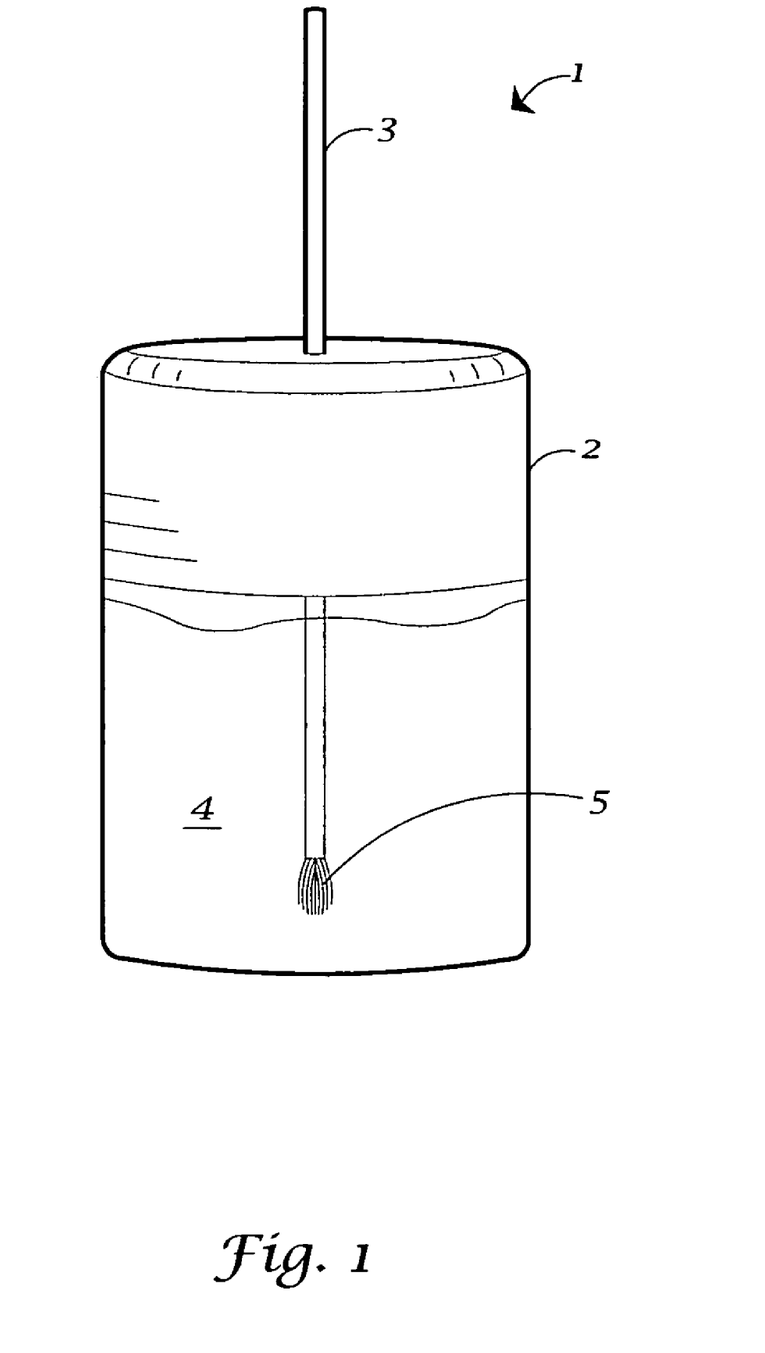
FIG. 1 is a schematic diagram of a container supporting an implement and enclosing an applicator and a dental composition having one or more volatile components in accordance with the invention.

The invention is now described in reference to FIGS. 1 through 12. With more particular reference to FIG. 1 is seen a unit dose packaging system 1, which includes enclosure 2, implement 3 and dental composition 4, which also includes polymerizable material. Enclosure 2 encloses the lower portion of implement 3 and dental composition 4. The lower portion of implement 3 is connected to applicator 5. Implement 3 is supported by enclosure 2. Enclosure 2 is made of a molded polymeric material, which retains volatile organic solvent, such as a copolymer of a cycloolefin and an olefin. Preferably dental composition 4 is hermetically sealed and stored in unit dose system 1 for at least 6 months effectively without loss of volatile organic solvent from dental composition 4.

Figure 2:
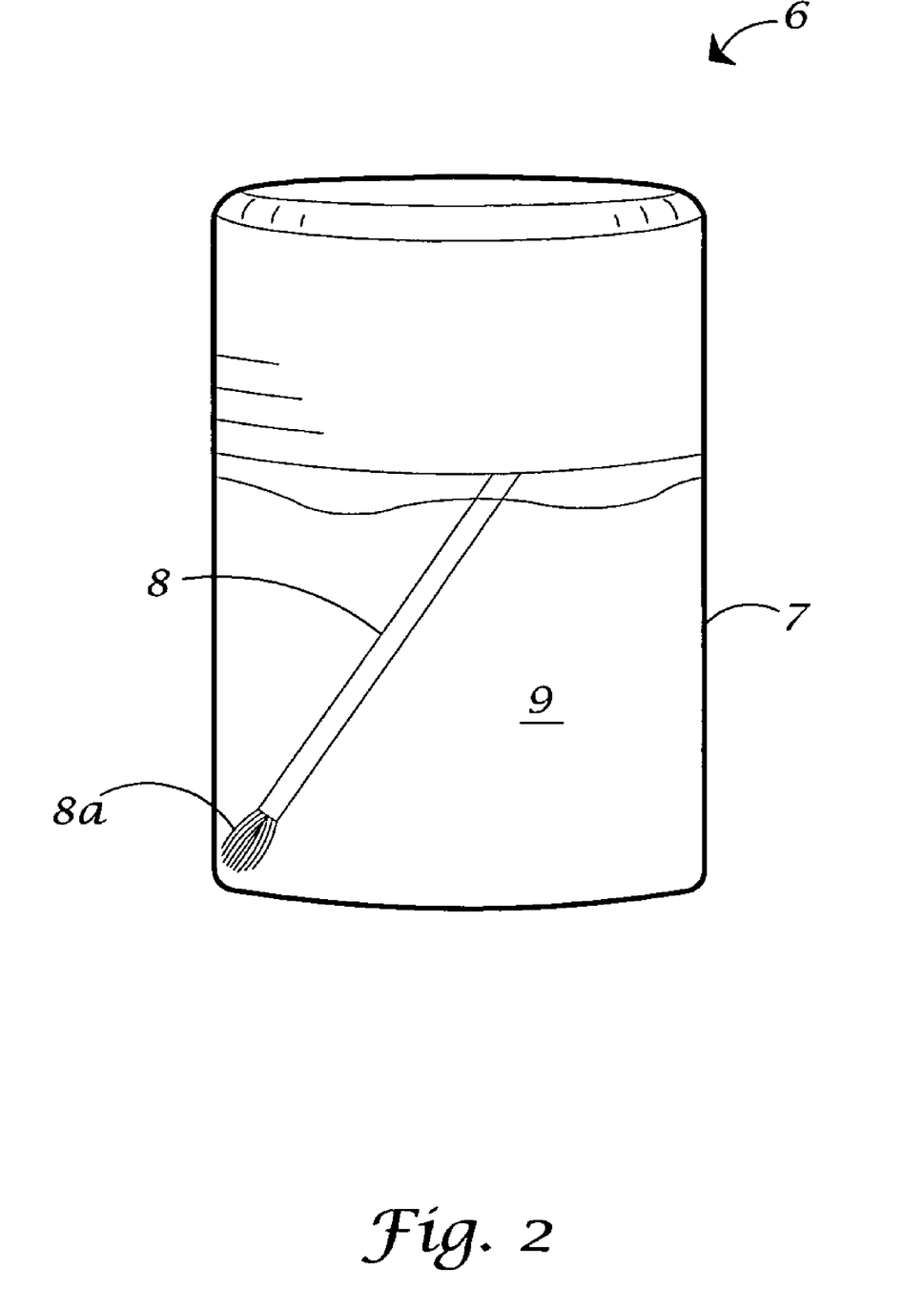
FIG. 2 is a schematic diagram of a container enclosing an implement having applicator and a dental composition having one or more volatile components in accordance with the invention.

With more particular reference to FIG. 2 is seen a unit dose packaging system 6, which includes enclosure 7, implement 8 and dental composition 9, which also includes polymerizable material. Enclosure 7 encloses implement 8 and dental composition 9. Implement 8 is connected to applicator 8A. Implement 8 is enclosed by enclosure 7. Enclosure 7 is made of a molded polymeric material, which retains volatile organic solvent, such as a copolymer of a cycloolefin and an olefin. Preferably dental composition 9 is hermetically sealed and stored in unit dose system 6 for at least 6 months effectively without loss of volatile organic solvent from dental composition 9.

Figure 3:
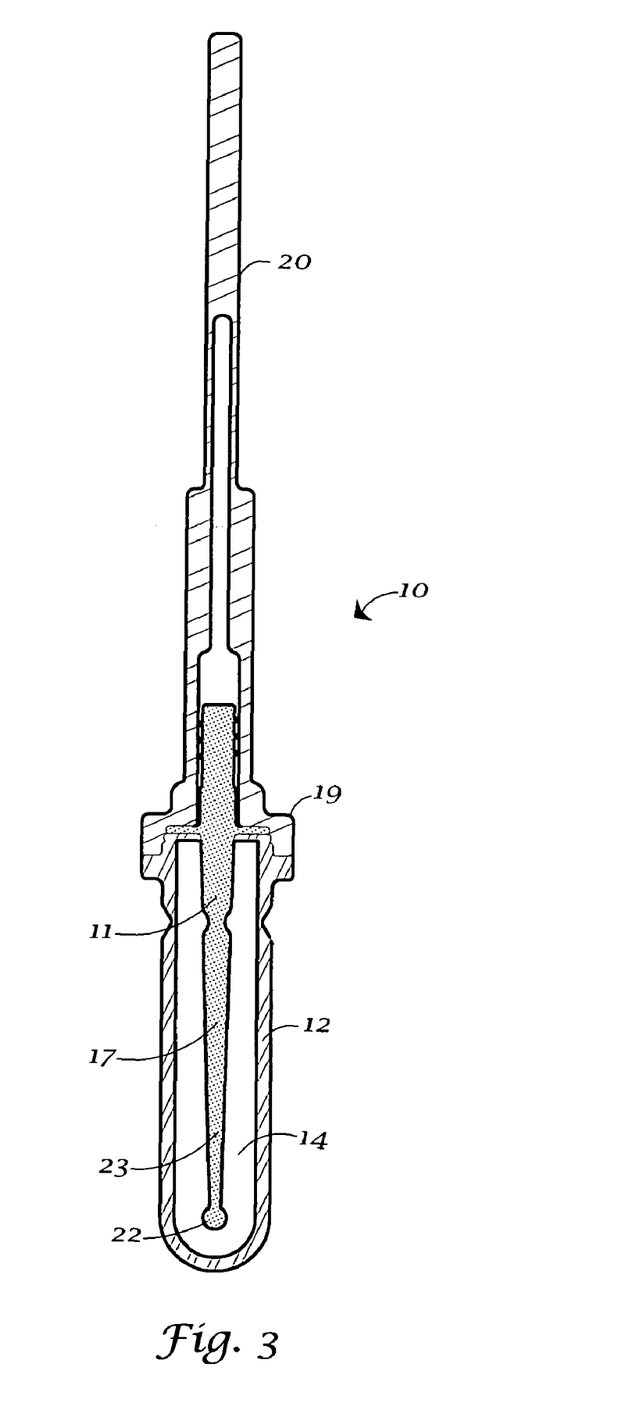
FIG. 3 is a cross-sectional side view of a container enclosing an applicator and a dental composition having one or more volatile components in accordance with the invention.
Figure 4:
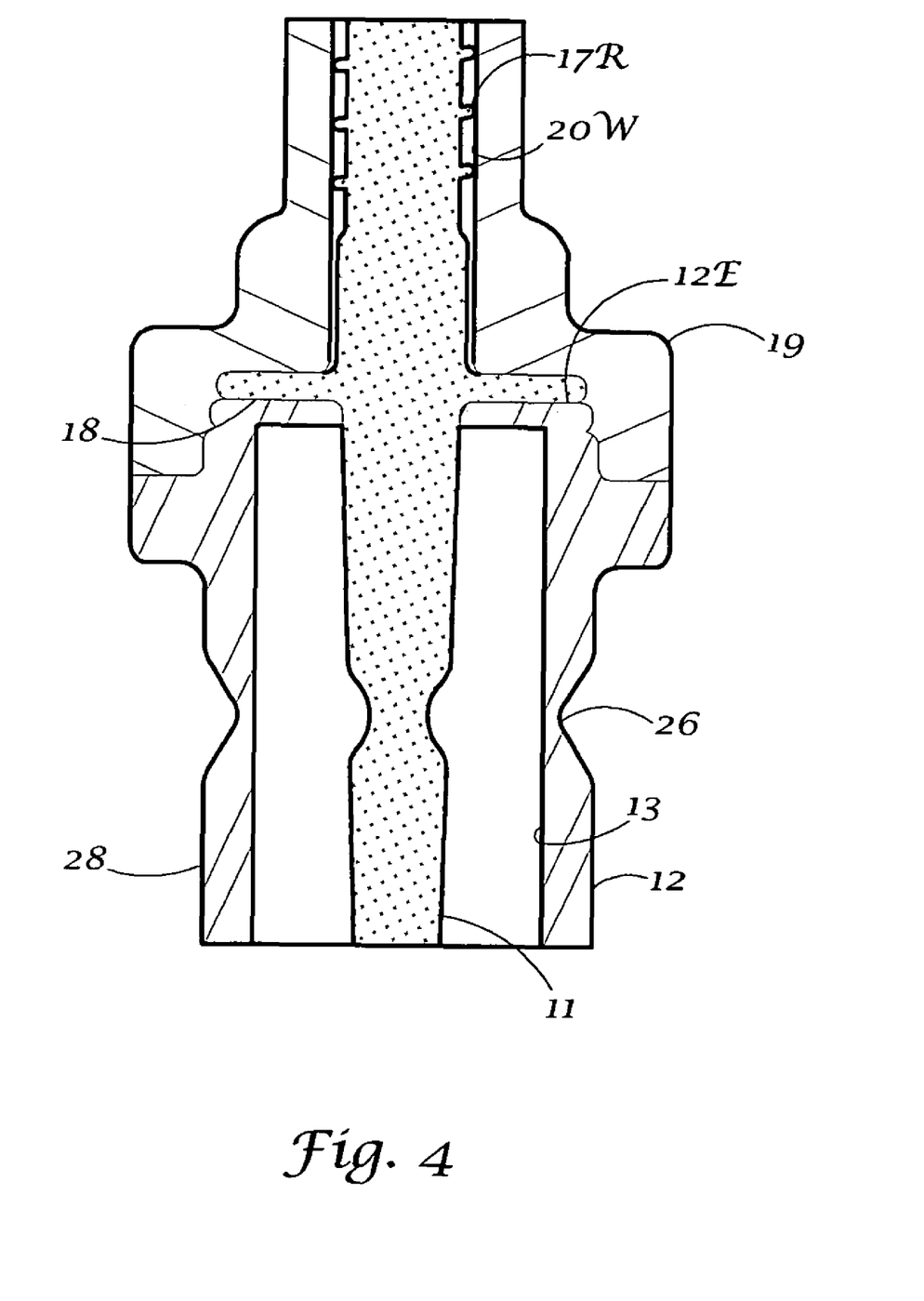
FIG. 4 is a partial cross-sectional side view of the container and implement arm shown in FIG. 3.

With more particular reference to FIGS. 3 and 4 is seen a unit dose packaging system 10, which includes implement 11 and container 12, and handle 20 which is integrally connected to connector flange 19. Container 12 has inner container wall 13 enclosing dental composition 14. Connector flange 19 fits over cover flange 18. Container 12 is adapted to break open along a line formed by a groove 26. When container 12 is broken, implement 11 is free to be used to remove portions of dental composition 14 from base portion 28 of container 12. After container 12 is broken, implement 11 has elongated arm 17, handle 20 and applicator 22. Cover flange 18 is integral with elongated arm 17. Elongated arm 17 and cover flange 18 are preferably integrally connected and made, for example by molding a flexible material, such as low density polyethylene or polypropylene. The upper portion of elongated arm 17 has ribs 17R, which are press fit into inner chamber wall 20W of handle 20. Container 12, connector flange 19 and handle 20 are made of a molded copolymer of a cycloolefin and an olefin. Dental composition 14 includes a volatile organic solvent. Dental composition 14 is effectively completely enclosed within molded copolymer of a cycloolefin and an olefin, which retains the volatile organic solvent. Preferably dental composition 14 also includes polymerizable material.

Container 12 has a cylindrical container wall. The applicator 22 is supported by elongated arm 17. Elongated arm 17 is supported by connector flange 19. Cover flange 18 seals one end of inner container wall 13. Cover flange 18 is sealed between end wall 12E of container 12 and inner capping wall 19C of connector flange 19. The cover flange 18 and inner container wall 13 enclose a chamber.

The container 12 is adapted to break open along a line formed by a groove 26 extending circumferentially around the outer surface of container 12. Container 12 has a first outer flange 42. Inner side wall 19B forms a hermetic seal with the first outer flange 42. Container 12 has a second outer flange 44. The closure is supported by and forms a hermetic seal with second outer flange 44. Handle 20 is connected through implement arm 17 to applicator 22. Container 12 is adapted to break open along groove 26. Before, during and after breaking open container 12, applicator 22 remains connected to handle 20. After container 12 is broken open the user holds handle 20 while dipping applicator 22 into dental composition 14 in the lower portion of the container 12. Then, while holding handle 20, the user applies the portion of dental composition 14 on applicator 22 to a dental tooth.

Figure 5:
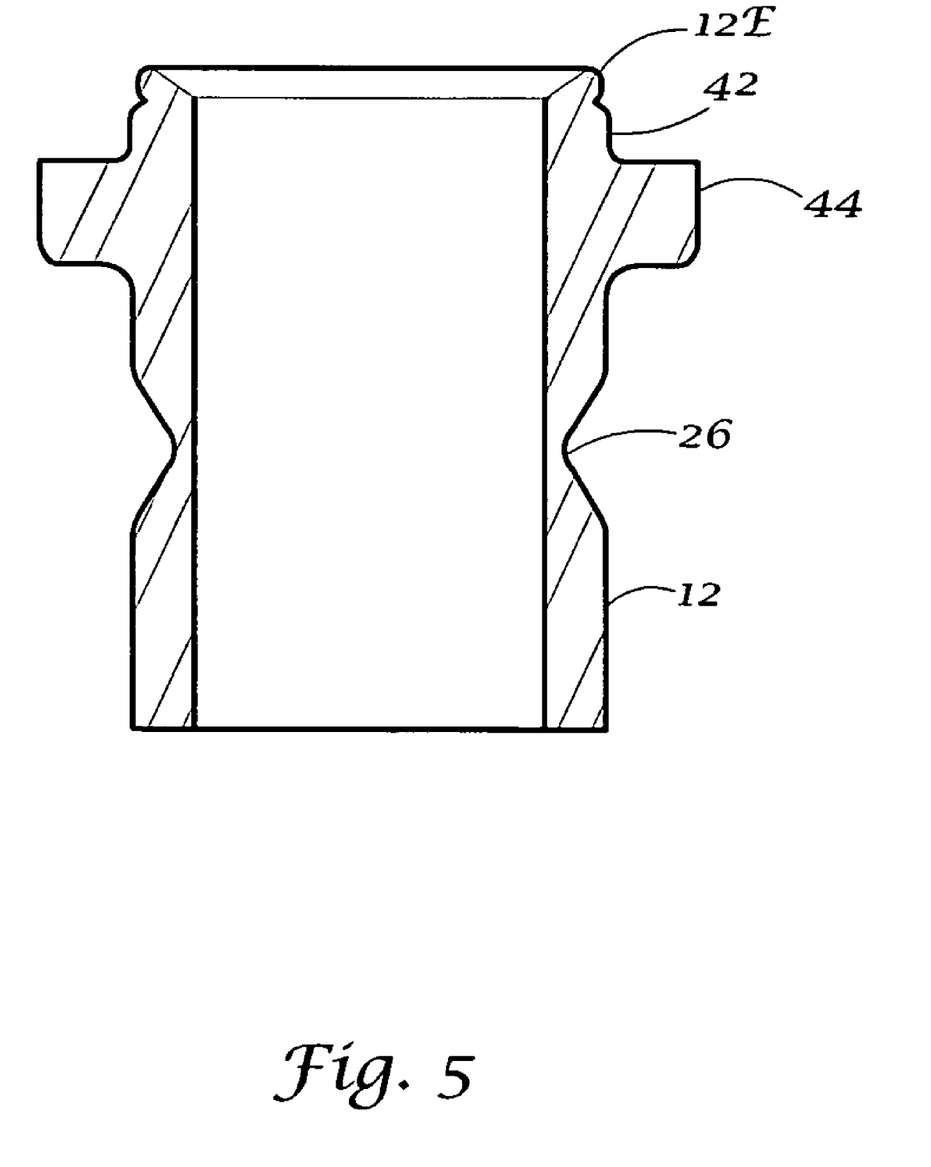
FIG. 5 is a partial cross-sectional side view of the container shown in FIG. 3.
Figure 6:
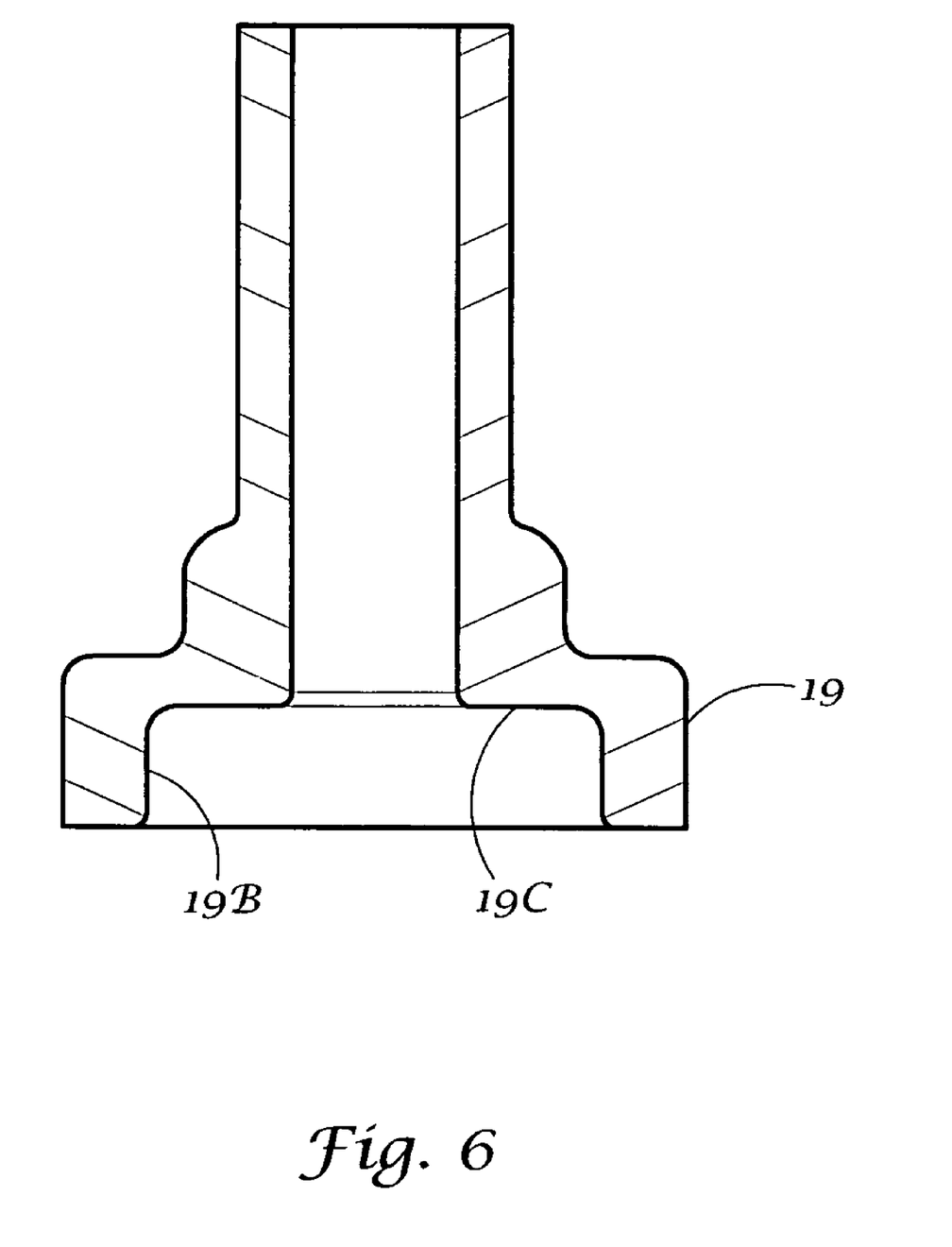
FIG. 6 is a partial cross-sectional side view of the handle and connector flange of the container shown in FIG. 3.

The dental composition in unit dose system 10 is stored for weeks, months or even years without significant loss of volatile organic solvent from dental composition 14. Preferably a dental composition is stored in unit dose system 10 for at least 6 months effectively without loss of volatile organic solvent from dental composition 14. Cover flange 18 is integrally connected to elongated arm 17, as shown in FIG. 4. Container 12 has end wall 12E, as shown in FIG. 5. Connector flange 19 has inner capping wall 19C, as shown in FIG. 6.

Figure 3A:
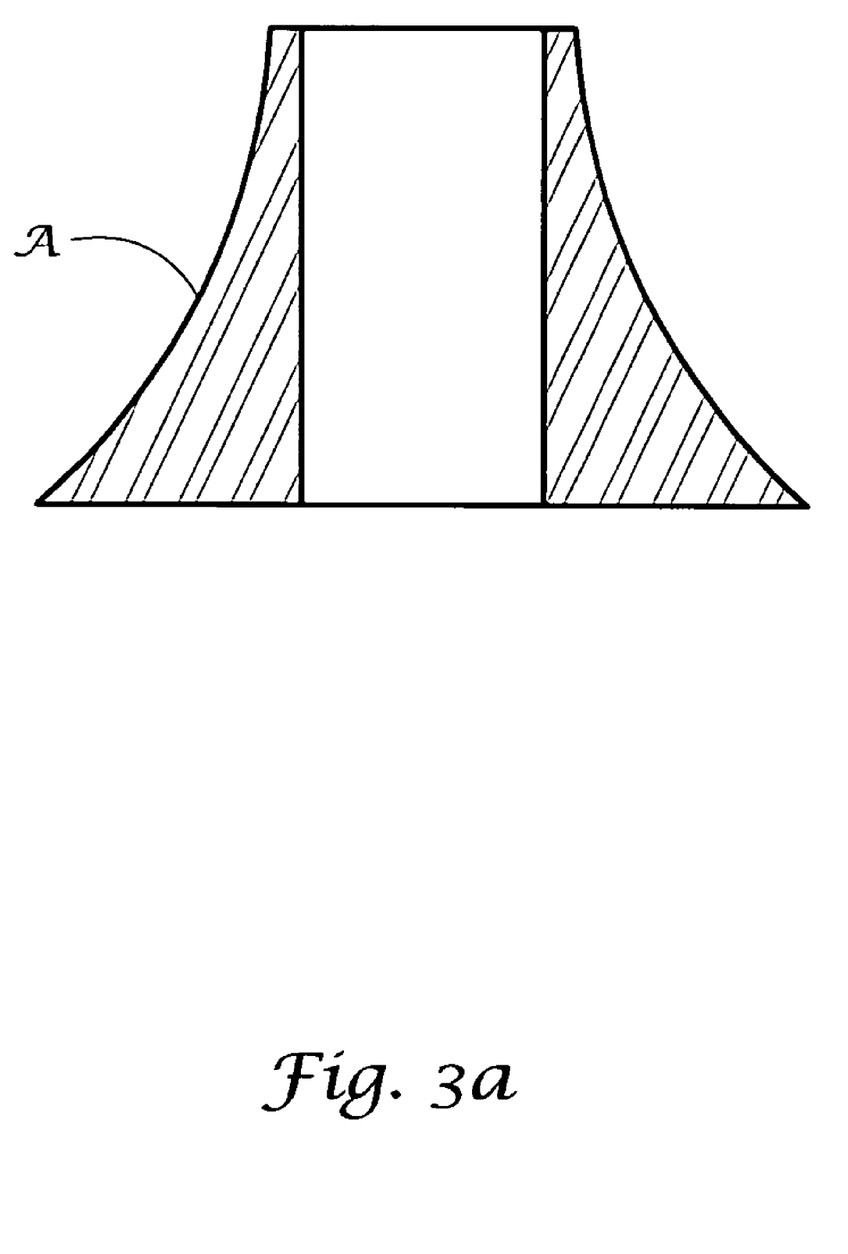
FIG. 3A is a cross-sectional side view of a holder.

In use, container 12 is preferably held vertically so that the volatile dental composition 14 is in base portion 28, below cover flange 18. Thus, base portion 28 of container 12 may be placed in holder H. Then, container 12 is broken at notch 26, and base portion 28 is placed in a holder, which is supported on a horizontal surface. Cover flange 18 is carried by handle 20. The user dispenses dental material on applicator 22 from the base portion 28, while the base portion 28 is supported in the holder. The user dispenses dental material by inserting applicator 22 into the broken open end of container 12. For example, while container 12 is supported in a holder supported on a horizontal surface. Applicator 22 is, for example, a bristle brush or a flocked element.

Handle 20 has a central handle axis. Container 12 has a central container axis. Elongated arm 17 has a central arm axis. The central handle axis, the central container axis and the central arm axis are coaxial.

Figure 7:
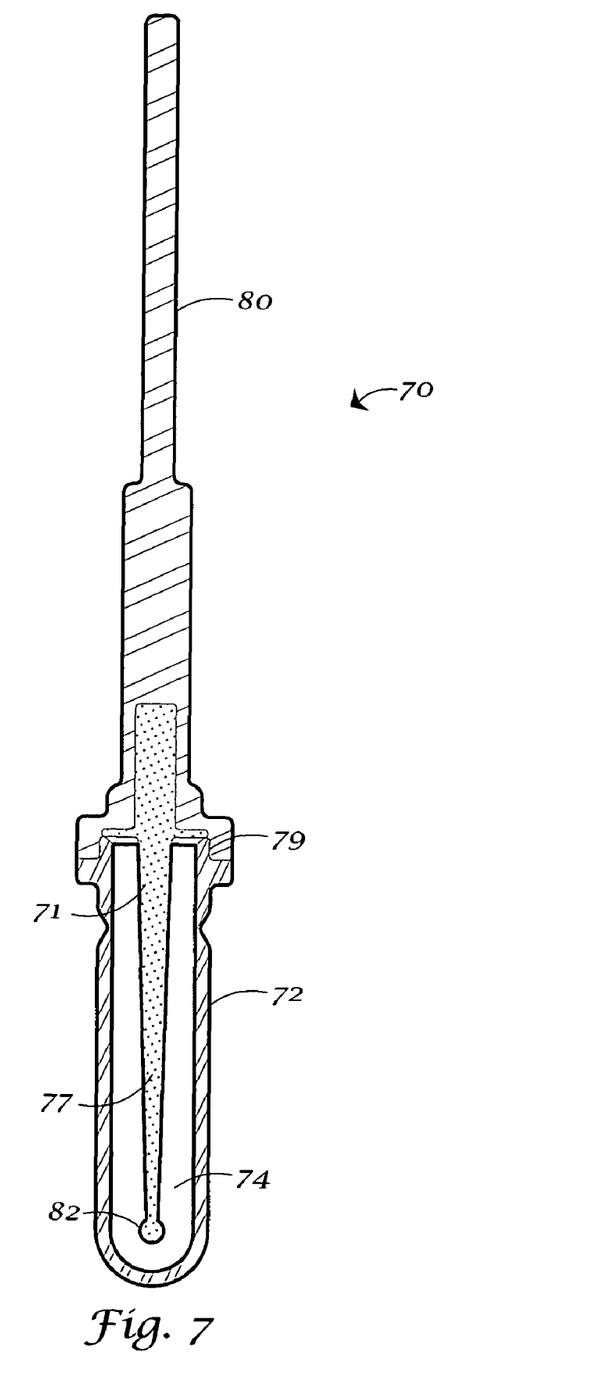
FIG. 7 is a cross-sectional side view of a container enclosing an applicator and a dental composition having one or more volatile components in accordance with the invention.
Figure 8:
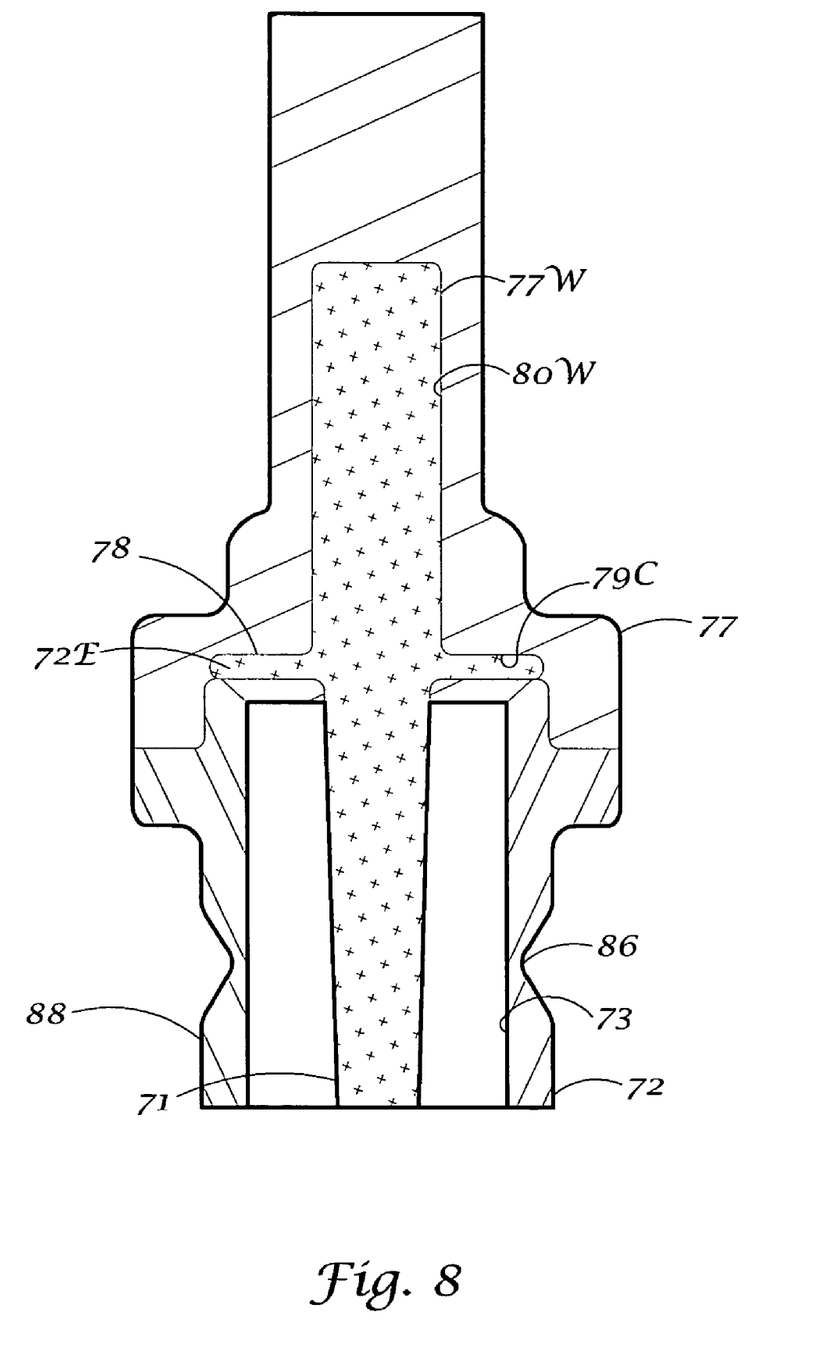
FIG. 8 is a partial cross-sectional side view of the container and implement arm shown in FIG. 7.

With more particular reference to FIGS. 7 and 8 is seen a unit dose packaging system 70, which includes implement 71 and container 72 and handle 80, which is integrally connected to connector flange 79. Container 72 has inner container wall 73 enclosing dental composition 74. Cover flange 78 is optional. Connector flange 79 fits over cover flange 78. Container 72 is adapted to break open along a line formed by a groove 86. When container 72 is broken, implement 71 is free to be used to remove portions of dental composition 74 from base portion 88 of container 72. After container 72 is broken, implement 71 has elongated arm 77, handle 80 and applicator 82. Cover flange 78 is integral with elongated arm 77. Elongated arm 77 and cover flange 78 are preferably integrally connected and made, for example by molding a flexible material, such as polypropylene. The upper portion of elongated arm 77 has outer wall 77W, which is injection molded into the chamber formed within inner chamber wall 80W. The upper portion of elongated arm 77 is sealed into inner chamber wall 80W of handle 80. Container 72, connector flange 79 and handle 80 are made of a molded copolymer of a cycloolefin and an olefin. Dental composition 74 includes a volatile organic solvent. Dental composition 74 is effectively completely enclosed within molded copolymer of a cycloolefin and an olefin, which retains the volatile organic solvent. Preferably dental composition 74 also includes polymerizable material.

Container 72 has a cylindrical container wall. The applicator 82 is supported by elongated arm 77. Elongated arm 77 is supported by connector flange 79. Cover flange 78 seals one end of inner container wall 73. Cover flange 78 is sealed between end wall 72E of container 72 and inner capping wall 79C of connector flange 79. The cover flange 78 and inner container wall 73 enclose a chamber. The container 72 is adapted to break open along a line formed by a groove 86 extending circumferentially around the container.

The dental composition in unit dose system 70 is stored for weeks, months or even years without significant loss of volatile organic solvent from dental composition 74. Preferably a dental composition is stored in unit dose system 70 for at least 6 months effectively without loss of volatile organic solvent from dental composition 74. Cover flange 78 is integrally connected to elongated arm 77. Container 72 has end wall 72E. Connector flange 79 has inner capping wall 79C.

In use, container 72 is preferably held vertically so that the volatile dental composition 74 is in base portion 88, below cover flange 78. Thus, base portion 28 of container 72 may be placed in a holder. Then, container 72 is broken at notch 86, and base portion 88 is placed in a holder, which is supported on a horizontal surface. The user dispenses dental composition 74 on applicator 82 from the base portion 88, while the base portion 88 is supported in the holder. The user dispenses dental material by inserting applicator 82 into the broken open end of container 72. For example, while container 72 is supported in a holder supported on a horizontal surface. Applicator 82 is, for example, a bristle brush or a flocked element.

Figure 9:
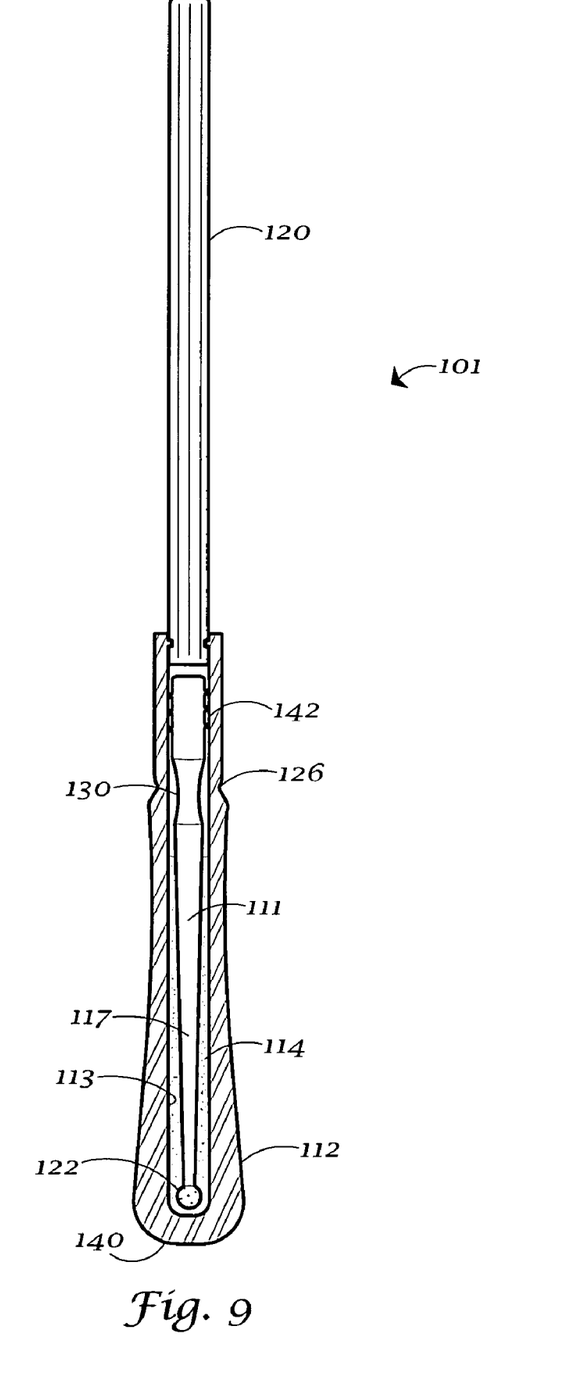
FIG. 9 is a cross-sectional side view of a container, applicator and composition in accordance with the invention.
Figure 10:
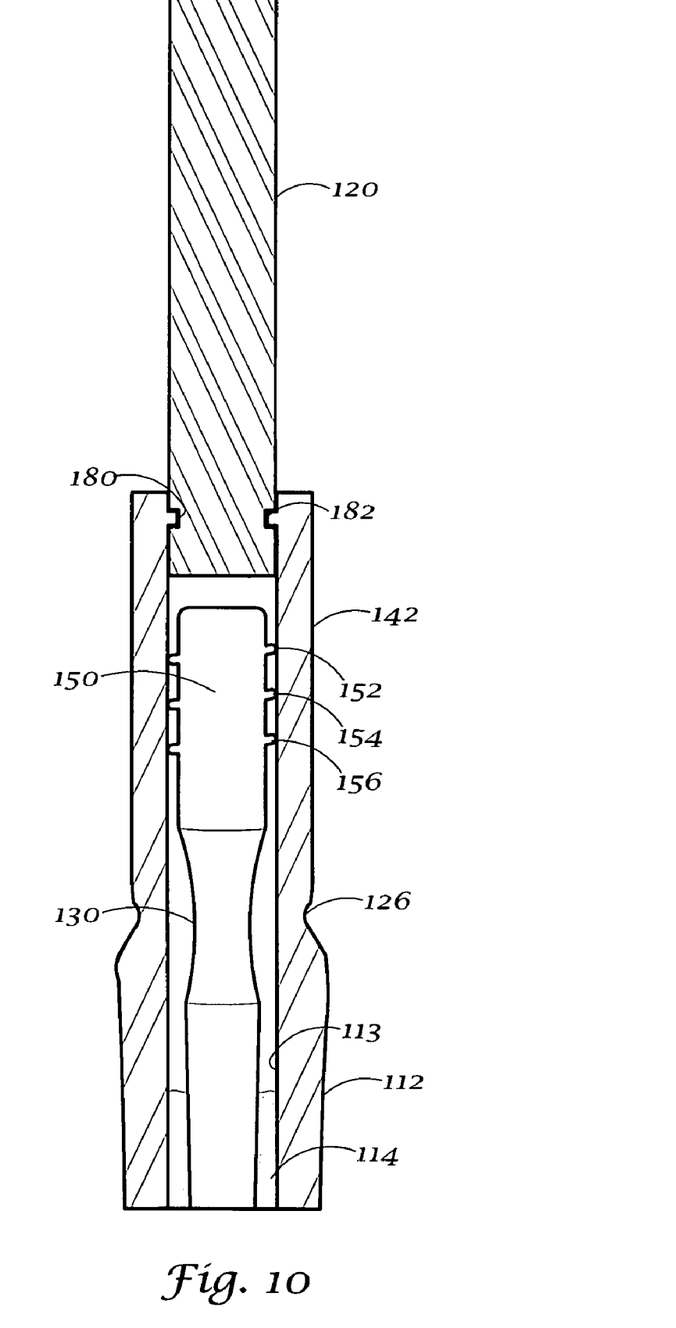
FIG. 10 is a partial cross-sectional side view of the container, implement and composition shown in FIG. 9.

With more particular reference to FIGS. 9 and 10 is seen a unit dose system 101 having implement 111, unit dose container 112 and handle 120. Container 112 has inner container wall 113 enclosing a dental composition 114. Implement 111 is supported by container 112. Implement 111 has elongated arm 117 and applicator 122. Applicator 122 is supported by elongated arm 117. Container 112 and handle 120 are made of a molded copolymer of a cycloolefin and an olefin. Elongated arm 117 is preferably made of a flexible material, such as polypropylene. Applicator 122 is, for example, a bristle brush or a flocked element. Dental composition 114 includes a volatile organic solvent. Preferably dental composition 114 also includes polymerizable material. Container 112 has a planar lower surface 140, which supports system 101 in an upright position on horizontal surfaces.

Inner container wall 113 of container 112 has an upper cylindrical portion 142. Upper portion 150 of elongated arm 117 has ribs 152, 154 and 156. Ribs 152, 154 and 156 are press fit into upper cylindrical portion 142 of container 112. Elongated arm 117 has readily bendable portion 130, which is adjacent to groove 126.

Locking flange 180 of container 112 extends into sealing groove 182 of handle 120. Container 112 is hermetically sealed through by ultrasonic sealing locking flange 180 to sealing groove 182 of handle 120. Hermetic sealing is carried out, for example, by thermal welding or ultrasonic welding. Container 112 is adapted to break open along a line formed by a groove 126 extending circumferentially around the container.

Dental composition 114 in unit dose system 101 is stored for weeks, months or years without significant loss of volatile organic solvent from dental composition 114. Preferably a dental composition is stored in unit dose system 101 for at least 6 months effectively without loss of volatile organic solvent from dental composition 114.

Figure 11:
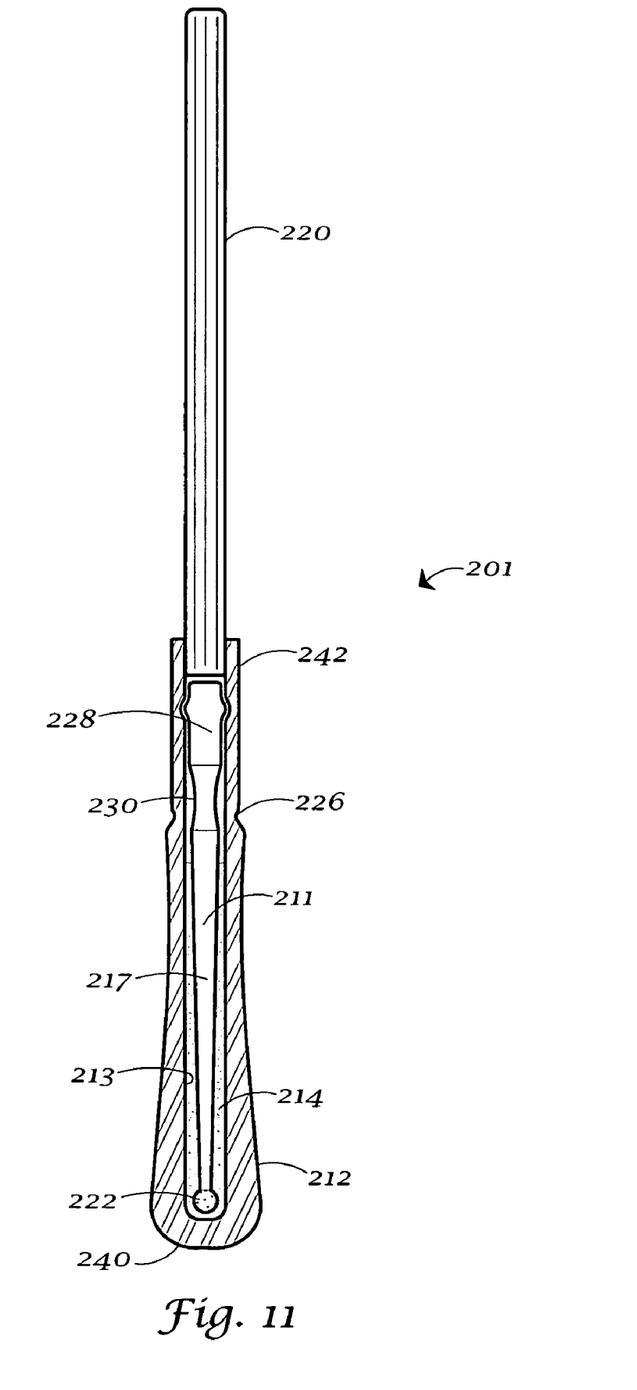
FIG. 11 is a cross-sectional side view of a container, applicator and composition in accordance with the invention.
Figure 12:
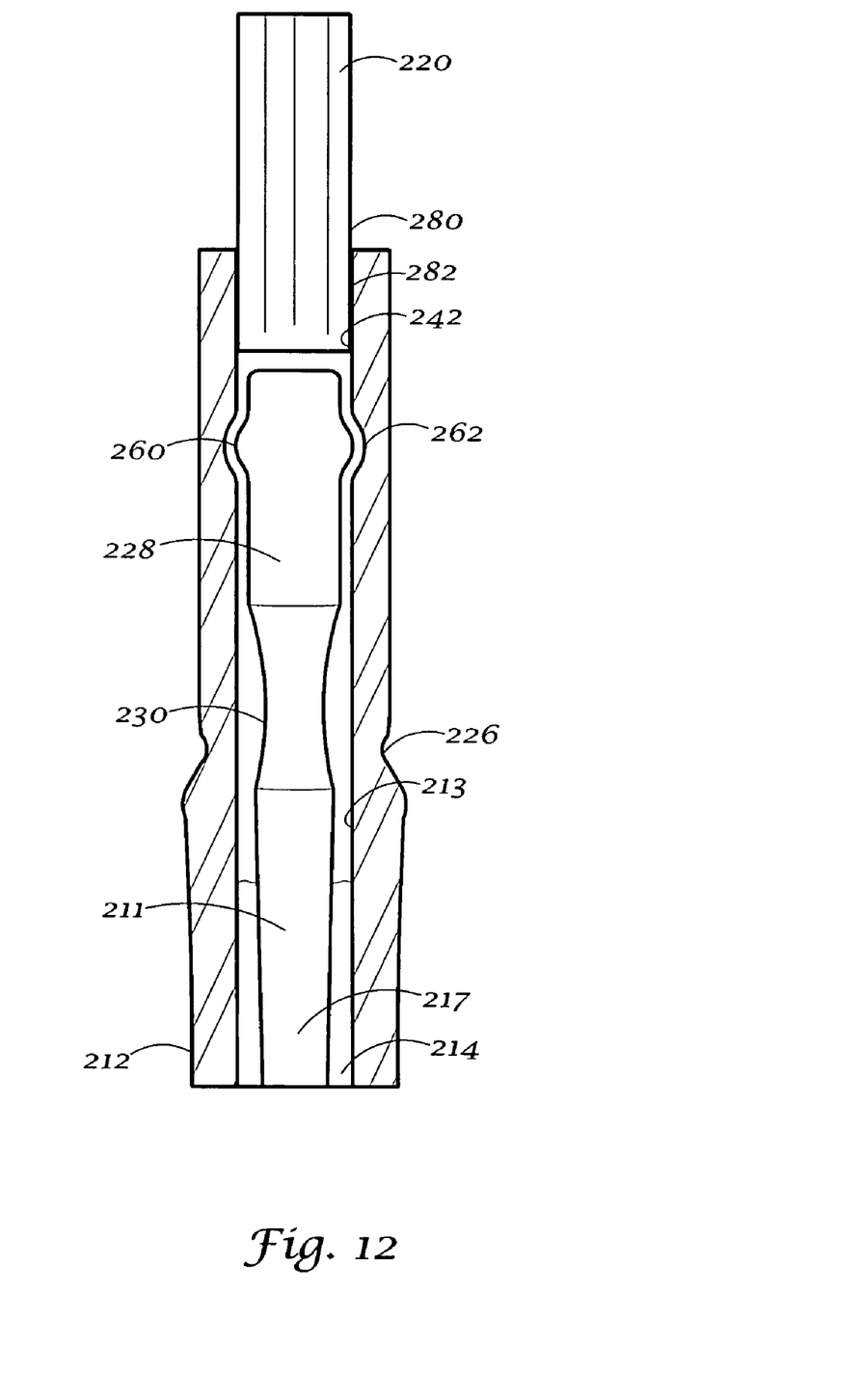
FIG. 12 is a partial cross-sectional side view of the container, implement and composition shown in FIG. 11.

With more particular reference to FIGS. 11 and 12 is seen a container 212, dental composition 214, implement 211 and handle 220. Implement 211 has an elongated arm 217 with an applicator 222 supported at its lower end. Readily bendable portion 230 of elongated arm 217 is adjacent to groove 226. Container 212 and handle 220 are made of a molded copolymer of a cycloolefin and an olefin. Dental composition 214 includes a volatile organic solvent. Container 212 is adapted to be broken at groove 226. Cylindrical portion 228 of implement 211 has snap ring 260, which forms a connection with upper portion 282 of inner container wall 213 along upper cylindrical portion 242. Snap ring 260 fits into and forms a connection to inner channel 262 in upper portion 282 of inner container wall 213.

Outer wall 280 of handle 220 is hermetically sealed with upper portion 282 of inner container wall 213 along upper cylindrical portion 242. Inner container wall 213 forms a hermetic seal with outer wall 280 of handle 220, for example, by thermal welding or ultrasonic welding.

Container 212 has a planar lower surface 240, which supports system 201 in an upright position on horizontal surfaces. Inner container wall 213 has an upper cylindrical portion 242. Elongated arm 217 is preferably made of a flexible material, such as polypropylene. Applicator 222 is, for example, a bristle brush or a flocked element. Elongated arm 217 has a wide cylindrical portion 228 above readily bendable portion 230, which is adjacent to groove 226.

Dental composition 214 in unit dose system 201 is stored for weeks, months or years without significant loss of volatile organic solvent from dental composition 214. Preferably a dental composition is stored in unit dose system 201 for at least 6 months effectively without loss of volatile organic solvent from dental composition 214.

Exemplary thermoplastic polymeric cycloolefin- olefin-copolymer for making containers and closures, such as handles, covers and connectors useful in accordance with the invention are disclosed in EP 407,870; EP 156,464 and EP 283,164. Thus each discloses copolymers of cycloolefin and olefin useful for making containers and closures such as covers, connectors and handles, for use in accordance with the invention. Open chain olefins, as used herein, refers to non-cyclic olefins and include linear open chain olefins, straight chain olefins, branched chain olefins and branched open chain olefins. Open chain olefins are not closed chain olefins or ring olefins. Linear open chain olefins are most preferred open chain olefins for use in making copolymer for use in accordance with the invention.

Single unit dosage, as used herein, refers to volumes of a dental composition between 0.01 and 1 ml. Volatile component, as used herein, refers to a component (of a dental composition) having vapor pressure more than that of water at 20° C. Volatile organic solvents, as used herein, refers to organic solvents, such as ethanol and acetone, which are more volatile than water at 20° C.

High permeability barrier capability for water, as used herein, refers to polymeric material having a water vapor permeability below 0.07 g $(mm)(m^2)(d^1)$ measured by DIN 53122 at 23° C. and 85 percent relative humidity. High penetration barrier capability of a polymeric material for water, as used herein, refers to a less than 3 percent by weight increase of a composition due to infusion of water through the polymeric material while the composition is enclosed in the polymeric material for at least two weeks at 37° C.

High penetration barrier capability for solvent of a polymeric material, as used herein, refers to less than 2 percent by weight loss of polar organic solvents from a composition having at least 5 percent by weight of polar organic solvent(s) while enclosed in the polymeric material for at least two weeks at 37° C.

High chemical resistance of polymeric material, as used herein, refers to polymeric material having both a less than 3 percent by weight increase of the polymeric material, and a less than 0.5 percent by weight decrease of the polymeric material while the polymeric material is immersed in water and/or solvent for at least two weeks at 37° C. A weight decrease of the polymeric material while enclosing a dental composition (and/or immersed in water and/or solvent) may be due to diffusion of components of the polymeric material from the polymeric material, and may cause contamination of the dental composition by components of the polymeric material. A weight increase of the polymeric material while enclosing-a dental composition and/or immersed in water and/or solvent may be due to infusion of water and/or solvent into the polymeric material, and may indicate that the polymeric material allows loss (or gain) of solvent from the dental composition and/or water contamination of a dental composition.

Dental compositions 4, 9, 14, 114 and 214 are enclosed by enclosures 2 and 7 and containers 12, 112 and 212 respectively. Dental compositions 4, 9, 14, 114 and 214 each include a volatile organic solvent. Dental compositions 4, 9, 14, 114 and 214 preferably include a polymerizable material. Dental compositions 4, 9, 14, 114 and 214 are stored for weeks, months or even years without significant loss of volatile organic solvent from enclosures 2 and 7 and containers 12, 112 and 212.

Enclosures 2 and 7 and containers 12, 112 and 212 and cover 18, and handles 120 and 220 are made of a copolymer of a cycloolefin and an olefin. Exemplary thermoplastic polymeric cycloolefin- olefin-copolymer useful for storage stable packaging of dental composition in accordance with the invention are disclosed in EP 407,870; EP 156,464 and EP 283,164. Thus, each discloses copolymers of cycloolefin and olefin useful for making containers, closures, implement arms, covers and connectors, for use in accordance with the invention.

Copolymer of cycloolefin and open chain olefin useful for storage stable packaging of dental composition in accordance with the invention have the following properties: thermoplasticity, suitable for injection-molding, high moisture-barrier capability, high barrier capability towards organic solvents, high chemical resistance, high rigidity, and suitability for sealing via thermal welding or ultrasonic welding. Preferred copolymers of cycloolefin and open chain olefin for use in accordance with a preferred embodiment of the invention are copolymers of norbornene and ethylene for example the norbornene-ethylene-copolymer sold by Ticona GmbH as Topas 6013 and Topas 8007. Both Topas 6013 and Topas 8007 norbornene-ethylene-copolymer have the following properties: thermoplasticity, can be processed on conventional injection molding machines; high moisture vapor barrier: permeability of 0.023 [Topas 8007] and 0.035 [Topas 6013] $(g)(mM/m^2)(24$ hours) at 23° C., 85% relative humidity, high barrier capability towards polar organic solvents such as acetone, high resistance towards water, strong acids and bases, and polar organic solvents such as methanol, ethanol and acetone, high rigidity: yield stress of 66 MPa, and tensile modulus of 3200 MPa.

In accordance with a preferred embodiment of the invention is provided a dental composition including a solvent and a polymerizable material enclosed by a container comprising a copolymer of a cycloolefin and an olefin. The dental composition is at least 1 percent by weight solvent, both before and after, storage at about 43° C. for one week. Preferably, the dental composition is at least 10 percent by weight solvent, both before and after, storage at about 43° C. for one week. Preferably, at least 99 percent of the solvent remains in the container after storage. More preferably, at least 99.5-99.8 percent of the solvent remains in the container after storage. Most preferably the solvent is a volatile organic solvent and at least 99.9 percent of the solvent remains in the container after storage.

The container disclosed herein may be molded and have an average wall thickness of from about 0.4 mm to about 6 mm.

The packaged dental composition disclosed herein may be stored at about 23° C. for at least one year and at least 80 percent of said volatile organic solvent remains in the container, or the packaged dental composition is stored at about 23° C. for at least two years and at least 90 percent of said volatile organic solvent remains in said container, or the packaged dental composition is stored at about 23° C. for at least two years and at least 95 percent of said volatile organic solvent remains in said container.

Further features of the packaged dental composition may be that the composition is at least 20 percent by weight acetone both before and after storage at about 23° C. for two years and at least 95 percent of said volatile organic solvent remains in said container after said storage, or that the packaged dental composition is at least 20 percent by weight acetone both before and after storage at about 23° C. for one year and at least 90 percent of said acetone remains in said container after said storage, or that the packaged dental composition is at least 40 percent by weight acetone both before and after storage at about 23° C. for two years and at least 95 percent of said volatile organic solvent remains in said container after said storage, or that the packaged dental composition is at least 40 percent by weight acetone both before and after storage at about 23° C. for one year and at least 90 percent of said acetone remains in said container after said storage, or that the packaged dental composition is at least 50 percent by weight acetone both before and after storage at about 23° C. for two years and at least 95 percent of said volatile organic solvent remains in said container after said storage, or that the packaged dental composition is at least 50 percent by weight acetone both before and after storage at about 23° C. for one year and at least 90 percent of said acetone remains in said container after said storage.

A stored enclosed dental product disclosed herein may be made by a process including enclosing an applicator and a dental composition having at least one volatile component in a container. The container may comprise a thermoplastic polymer having a high chemical resistance and a high permeability barrier capability for water. Storing the dental composition in the container for at least two weeks at 37° C. and after the two weeks at least 90 percent of said volatile component remains in the dental composition in the container.

The stored enclosed dental product disclosed herein made by the process including enclosing an applicator and a dental adhesive composition having a volatile organic solvent in a container. The container may comprise a thermoplastic copolymer of a cycloolefin and an open chain olefin. The volatile organic solvent is effectively retained in the dental composition while storing the dental composition in the container for at least 1 week at about 23° C. The solvent may include a polar organic solvent, and the copolymer of a cycloolefin and an open chain olefin may have a high permeability barrier capability for water and high chemical resistance, and at least 90 percent of said polar organic solvent remains in the dental composition in the container while stored at about 23° C. for about two years. The dental composition may include at least 15 percent by weight of the solvent, and at least 99.8 percent of the solvent remains in the dental composition in the container after the storage. The dental composition may bond to dentin with effectively the same amount of bond strength before and after storage in the container.

Various alterations and modifications of the invention will be apparent to those of ordinary skill in the art without departing from the scope and spirit of this invention. Accordingly, it should be understood that the invention is not limited to the illustrative embodiments set forth herein.

What is claimed is:

1. A storage stable enclosed dental composition, comprising:
    a container, an implement and a dental composition,
    said implement having an elongated arm and an applicator, said applicator being supported by said arm,
    said applicator and said dental composition being enclosed by said container, said container comprising a copolymer of a cycloolefin and an open chain olefin,
    said dental composition, comprising at least 1 percent by weight of volatile organic solvent, at least 99 percent of said solvent remaining in said dental composition in said container after storage at about 43° C. for one week,
    further comprising a closure, and wherein said container has inner and outer wall faces, and said container outer wall face has a groove, said applicator is supported by said closure, said closure having a cover and a connector, said connector having an inner and end wall faces, said connector inner wall face sealing and engaging said container end outer wall face,
    said cover and said container inner wall face enclosing a chamber, said container wall having a first outer flange, said connector inner wall face sealing and engaging said first outer flange.

2. The storage stable enclosed dental composition of claim 1 wherein said dental composition further comprises a polymerizable material.

3. The storage stable enclosed dental composition of claim 1 wherein said volatile organic solvent comprises at least 10 percent by weight of said dental composition.

4. The storage stable enclosed dental composition of claim 1 wherein said container is molded and has an average wall thickness of from about 0.4 mm to about 6 mm.

5. The storage stable enclosed dental composition of claim 1 wherein said packaged dental composition is stored at about 23° C. for at least one year and at least 80 percent of said volatile organic solvent remains in said container.

6. The storage stable enclosed dental composition of claim 1 wherein said packaged dental composition is stored at about 23° C. for at least two years and at least 90 percent of said volatile organic solvent remains in said container.

7. The storage stable enclosed dental composition of claim 1 wherein said packaged dental composition is stored at about 23° C. for at least two years and at least 95 percent of said volatile organic solvent remains in said container.

8. The storage stable enclosed dental composition of claim 1 wherein said volatile organic solvent comprises acetone.

9. The storage stable enclosed dental composition of claim 1 wherein said packaged dental composition is at least 20 percent by weight acetone both before and after storage at about 23° C. for two years and at least 95 percent of said volatile organic solvent remains in said container after said storage.

10. The storage stable enclosed dental composition of claim 1 wherein said packaged dental composition is at least 20 percent by weight acetone both before and after storage at about 23° C. for one year and at least 90 percent of said acetone remains in said container after said storage.

11. The storage stable enclosed dental composition of claim 1 wherein said packaged dental composition is at least 40 percent by weight acetone both before and after storage at about 23° C. for two years and at least 95 percent of said volatile organic solvent remains in said container after said storage.

12. The storage stable enclosed dental composition of claim 1 wherein said packaged dental composition is at least 40 percent by weight acetone both before and after storage at about 23° C. for one year and at least 90 percent of said acetone remains in said container after said storage.

13. The storage stable enclosed dental composition of claim 1 wherein said packaged dental composition is at least 50 percent by weight acetone both before and after storage at about 23° C. for two years and at least 95 percent of said volatile organic solvent remains in said container after said storage.

14. The storage stable enclosed dental composition of claim 1 wherein said packaged dental composition is at least 50 percent by weight acetone both before and after storage at about 23° C. for one year and at least 90 percent of said acetone remains in said container after said storage.

15. The storage stable enclosed dental composition of claim 1, wherein said container wall has a second outer flange.

16. The storage stable enclosed dental composition of claim 15, wherein said elongated arm extends through said container and said elongated arm is supported by said container.

17. The storage stable enclosed dental composition of claim 15, wherein said closure is supported by at least one outer flange.

18. The storage stable enclosed dental composition of claim 1 wherein said container has an outer wall with a groove, and said container wall is adapted to break open along said groove.

19. The storage stable enclosed dental composition of claim 18, wherein said groove forms a line extending circumferentially around said container.

20. A stored enclosed dental product made by the process comprising:
enclosing an applicator and a dental composition having at least one volatile component in a container, said container comprising thermoplastic polymer having a high chemical resistance and a high permeability barrier capability for water, and
storing said dental composition in said container for at least two weeks at 37° C. and after said two weeks at least 90 percent of said volatile component remains in said dental composition in said container,
wherein the container comprises a closure, and wherein said container has inner and outer wall faces, and said container outer wall face has a groove, said applicator is supported by said closure, said closure having a cover and a connector, said connector having an inner and end wall faces, said connector inner wall face sealing and engaging said container end outer wall face,
said cover and said container inner wall face enclosing a chamber, said container wall having a first outer flange, said connector inner wall face sealing and engaging said first outer flange.

21. A stored enclosed dental product made by the process comprising:
enclosing an applicator and a dental adhesive composition comprising volatile organic solvent in a container, said container comprising a thermoplastic copolymer of a cycloolefin and an open chain olefin, and effectively retaining said volatile organic solvent in said dental composition while storing said dental composition in said container for at least 1 week at about 23° C.
wherein the container comprises a closure, and wherein said container has inner and outer wall faces, and said container outer wall face has a groove, said applicator is supported by said closure, said closure having a cover and a connector, said connector having an inner and end wall faces, said connector inner wall face sealing and engaging said container end outer wall face,
said cover and said container inner wall face enclosing a chamber, said container wall having a first outer flange, said connector inner wall face sealing and engaging said first outer flange.

22. The product of claim 21 wherein said dental composition is a single unit dosage and said thermoplastic polymer has a high chemical resistance, a high penetration barrier capability for water, high penetration barrier capability for solvent and a high permeability barrier capability for water.

23. The stored enclosed dental product of claim 21 wherein said solvent comprises a polar organic solvent, said copolymer of a cycloolefin and an open chain olefin has a high permeability barrier capability for water and high chemical resistance, and at least 90 percent of said polar organic solvent remains in said dental composition in said container while stored at about 23° C. for about two years.

24. The stored enclosed dental product by the process of claim 23 wherein said dental composition comprises at least 1 percent by weight of said solvent, and at least 99 percent of said solvent remains in said dental composition in said container after said storage.

25. The stored enclosed dental product by the process of claim 23 wherein said dental composition comprises at least 15 percent by weight of said solvent, and at least 99.8 percent of said solvent remains in said dental composition in said container after said storage.

26. The stored enclosed dental product by the process of claim 23 wherein said dental composition bonds to dentin with effectively the same amount of bond strength before and after said storing.

27. The stored enclosed dental product by the process of claim 21 further comprising a handle, said handle being supported by and connected to said container.

28. The stored enclosed dental product by the process of claim 27 wherein said handle is connected through an implement arm to said applicator, and said container has an outer wall with a groove, and said container wall is adapted to break open along said groove, while said applicator remains connected to said handle.

29. The stored enclosed dental product by the process of claim 28 wherein said implement arm is low density polyethylene or polypropylene.

* * * * *